(12) United States Patent
Aldaz

(10) Patent No.: US 12,723,971 B2
(45) Date of Patent: Sep. 1, 2026

(54) METHOD AND APPARATUS FOR MEASURING ABSORPTION COEFFICIENT OF A MEDIUM

(71) Applicant: BarrIQ Inc., Pleasanton, CA (US)

(72) Inventor: Rafael I. Aldaz, Pleasanton, CA (US)

(73) Assignee: BARRIQ INC., Pleasanton, CA (US)

( * ) Notice: Subject to any disclaimer, the term of this patent is extended or adjusted under 35 U.S.C. 154(b) by 0 days.

(21) Appl. No.: 19/370,565

(22) Filed: Oct. 27, 2025

(65) Prior Publication Data

US 2026/0118259 A1 Apr. 30, 2026

Related U.S. Application Data

(60) Provisional application No. 63/713,041, filed on Oct. 28, 2024.

(51) Int. Cl.
*G01N 21/03* (2006.01)
*G01N 21/31* (2006.01)
(Continued)

(52) U.S. Cl.
CPC ......... *G01N 21/0303* (2013.01); *G01N 21/31* (2013.01); *G01N 21/3504* (2013.01);
(Continued)

(58) Field of Classification Search
CPC .... G01N 21/0303; G01N 21/31; G01N 21/59; G01N 21/255; G01N 21/3504; G01N 21/3577; G01N 21/33; G01N 21/3581; G01N 21/359; G01N 21/3103; G01N 21/35; G01N 2201/066; G01N 2201/0668; G01N 2201/0662; G01N 2201/0666; G01N 2021/3129; G01N 2021/3133;
(Continued)

(56) References Cited

U.S. PATENT DOCUMENTS 2,761,067 A * 8/1956 Troy, Jr. ............... G01N 21/314 250/210
3,526,462 A * 9/1970 Mccurdy ........... G01N 21/0303 250/343

(Continued)

FOREIGN PATENT DOCUMENTS

CA 2894104 A1 * 12/2010 ......... G01N 21/3577
CA 2988658 C * 7/2023 ........... A61B 5/1455

(Continued)

*Primary Examiner* — Gordon J Stock, Jr.
(74) *Attorney, Agent, or Firm* — Rupak Nag

(57) ABSTRACT

The present invention discloses a method to optically measure the absorption coefficient of a liquid or gas medium, without affecting the medium. Such absorption spectrum can be utilized to quantify the chemical components of the medium, or other metrics such as color or signature of the medium. The method acknowledges the possible drifts in the optical components of the system with time and measures the absorption coefficient independently of the state of the optical components. Therefore, there is no need to calibrate the system or take reference measurements. The method presented can be implemented cost effectively, designed in compact systems, and is energy efficient, thus, meeting the stringent challenges of spaced constrained remote systems such as aging wine barrels.

9 Claims, 2 Drawing Sheets

(51) Int. Cl.
*G01N 21/3504* (2014.01)
*G01N 21/3577* (2014.01)
*G01N 33/14* (2006.01)

(52) U.S. Cl.
CPC ....... *G01N 21/3577* (2013.01); *G01N 33/146* (2013.01); *G01N 2201/0662* (2013.01); *G01N 2201/0668* (2013.01)

(58) Field of Classification Search
CPC .... G01N 33/146; G01N 33/143; G01N 33/14; G01J 3/42; G01J 2003/421; G01J 2003/423; G01J 2003/425
See application file for complete search history.

(56) References Cited

U.S. PATENT DOCUMENTS 3,843,269 A * 10/1974 Hohberg ................ G01N 21/59 250/564
4,023,909 A * 5/1977 Ross ...................... G01N 21/85 250/575
4,648,713 A * 3/1987 Borer ................. G01N 21/0303 356/428
4,687,337 A * 8/1987 Stewart ................ G01N 21/534 250/575
5,268,736 A * 12/1993 Prather ............. G01N 21/0303 250/576
5,281,817 A * 1/1994 Yelderman ......... G01N 21/3504 250/343
5,287,168 A * 2/1994 Poucher ............. G01N 21/8507 250/576
6,342,948 B1 * 1/2002 Gilby ..................... G01N 30/74 356/440
6,643,016 B2 * 11/2003 Garver ................... G01N 21/33 356/312
7,796,261 B2 * 9/2010 Juhl ...................... G01N 21/31 356/440
7,826,050 B2 * 11/2010 DiFoggio ........... G01N 21/0303 356/432
7,847,944 B2 * 12/2010 Buettner ............. G01N 21/274 356/243.1
7,920,252 B2 * 4/2011 Hu ........................ G01N 21/31 356/73
8,873,057 B2 * 10/2014 Born .................. G01N 29/2418 385/33
8,908,184 B2 * 12/2014 Bernhard ........... G01N 21/8507 356/432
9,404,851 B2 * 8/2016 Shih ................... G01N 33/6854
9,568,458 B2 * 2/2017 Smeeton ................ G01N 21/59
9,939,373 B2 * 4/2018 Salemo ............. G01N 21/0303
10,551,311 B2 * 2/2020 Smith .................... G01N 21/59
10,677,724 B2 * 6/2020 Foord ................ G01N 21/0303
12,000,775 B2 * 6/2024 Duff ..................... G01N 21/274
12,366,528 B2 * 7/2025 Ehring ................... G01N 21/45
12,379,251 B2 * 8/2025 Fantini ...................... G01J 3/42
12,411,043 B2 * 9/2025 Muller ...................... G01J 3/42
12,422,356 B2 * 9/2025 Muller ............... G01N 21/0303
2002/0036266 A1 * 3/2002 Dreyer ............... G01N 21/3504 250/343
2009/0027676 A1 * 1/2009 Model .................... G01N 21/59 356/436
2009/0209836 A1 * 8/2009 Niwayama ......... A61B 5/14551 600/324
2013/0003045 A1 * 1/2013 Wilkins ............... G01N 21/031 356/402
2014/0176952 A1 * 6/2014 Floquet .................. G01N 21/17 356/440
2015/0268095 A1 * 9/2015 Kovacich .................. G01J 3/10 356/437
2016/0069803 A1 * 3/2016 Sano ...................... G01N 21/85 356/440
2016/0178508 A1 * 6/2016 Ramsteiner .......... G01N 21/314 356/432
2021/0383571 A1 * 12/2021 Tomizawa ............... A61B 5/00
2022/0252505 A1 * 8/2022 Hansen ................ G01N 21/274
2022/0268628 A1 * 8/2022 Gantier ..................... G01J 3/42
2023/0375468 A1 * 11/2023 Muller ............... G01N 21/0303
2025/0102426 A1 * 3/2025 Yeremi ................... G01J 3/433

FOREIGN PATENT DOCUMENTS

CN 100590418 C * 2/2010
CN 101852727 A * 10/2010
CN 107179283 A * 9/2017 ............. G01N 21/64
CN 107451413 A * 12/2017 ............. G16Z 99/00
CN 109187426 A * 1/2019 ............. G01N 21/39
CN 113176222 A * 7/2021 ............. G01N 21/31
DE 2810117 A1 * 9/1979
EP 634642 A1 * 1/1995
GB 2541351 A * 2/2017 ........... G01N 21/274
JP H07128229 A * 5/1995
JP H08114541 A * 5/1996
JP 2003035662 A * 2/2003
JP 2003035663 A * 2/2003
JP 2010175342 A * 8/2010 ......... G01N 21/0303
KR 102100822 B1 * 4/2020 ......... G01N 21/5907
NO 118464 B * 12/1969 ................ G01J 3/28
RU 2532585 C2 * 11/2014 ................ G01J 3/51
WO WO-9832003 A1 * 7/1998 ......... G01N 33/2829
WO WO-2004025281 A1 * 3/2004 ......... G01N 21/0303
WO WO-2007065772 A1 * 6/2007 ......... G01N 21/0303
WO WO-2007126389 A1 * 11/2007 ......... G01N 21/0303
WO WO-2025247925 A1 * 12/2025 ................ G01J 3/10

* cited by examiner

METHOD AND APPARATUS FOR MEASURING ABSORPTION COEFFICIENT OF A MEDIUM

CROSS-REFERENCE TO RELATED APPLICATION

This application claims priority from U.S. Provisional Application No. 63/713,041, filed Oct. 28, 2024 titled "Optical-based chemical sensor requiring minimal calibration", the entire disclosure of which are hereby expressly incorporated by reference herein in its entirety.

FIELD OF THE INVENTION

The present disclosure generally relates to methods and apparatus for detecting chemicals in a medium utilizing an optical sensor. More specifically, it relates to an optical sensor apparatus and related methods that measures chemicals, such as sulfites, and other characteristics of the medium and does so with minimal to no manual intervention or calibration of the optical sensor.

BACKGROUND

A significant operating expense for wine makers, in particular high-volume vinters, is measuring and managing the amount of free $SO_2$, sulfites in the wine which functions as a preservative. There are federal regulations that dictate the amount of sulfite that can be in wine and, generally, wine makers want to minimize sulfites in their wine since it is undesirable by consumers. It functions similar to a preservative by killing bacteria in the wine however one side effect, for example, is that when there is too much sulfite, consumers can get headaches or other undesirable side effects.

However, a certain amount of sulfite is needed in the wine to kill bacteria and preserve the wine as it ages. And sulfite levels in an enclosed barrel drops over time. The key is to maintain this minimal sulfite amount necessary for preservation over a period of months and often years. Wine makers must check the sulfite levels in the wine stored in barrels and replenish if needed, for example, every six weeks.

The overall objective is to decrease operating costs for the wine maker and to improve the quality of wine through more efficient management of sulfites. The apparatus of the present invention enables wine makers to achieve these goals. In addition, they are able to save a full optical spectrum of the wine to determine the chemical composition or wine "DNA" and possibly replicate it at a later time.

There are generally four stages in wine making: harvest, fermentation, aging, and bottling. Monitoring and managing sulfites take place in the aging stage. One current method of measuring sulfites in a wine barrel is chemical-based and is generally performed by taking a sample and chemically testing in a laboratory. When it is determined that the sulfite level in the wine has dropped below the minimum threshold amount, the barrel needs to be opened in order to inject more $SO_2$. When measuring, wine makers often take a composite of, for example, measurements from five barrels for every 100 and make an informed estimate that all 100 barrels need a similar injection of $SO_2$ (e.g., the maximum needed in those five) for the composite. Wine samples from the five barrels must be sent to a laboratory outside or can be in the winery. And every time a barrel is opened, oxygen is introduced into the barrel which is also undesirable.

Other methods to measure wine are optical-based and use a wavelength detection region between 800 nm and 1600 nm. As noted below, this is not optimal for $SO_2$ detection. And such cork sensors are expensive to purchase and maintain. Another optical-based method extracts wine from the barrel, uses an acid to evaporate the sulfites, and optically measures the density of the cloud to determine the density of sulfites in the wine. Obviously, this method can only be done outside of the barrel.

With any optical measurements, there are frequent calibrations necessary to obtain accurate measurements. Factory calibrations don't account for drifts in the optical components, which lead to erroneous measurements in the field. More complex systems can add extra components to calibrate prior to measurement, thereby accounting for drifts in the system over time or use. However, these systems are bulky and costly and, thus not recommended for devices inside the barrel; they are and limited to systems outside the barrel.

As a result, wine makers take different steps to manage the amount of free sulfite in wine stored in a wine barrel.

One objective is to avoid removing barrels off a rack in order to measure sulfite. Another objective is to avoid having to take the cork or closure apparatus out of the barrel (which exposes the wine to oxygen and contaminants) but still be able to measure sulfite levels. In addition, it would be desirable to measure temperature, humidity, and pressure within the barrel, barrel ullage, and pH levels. It would also be desirable to not have to open the barrel in order to dispense wine or $SO_2$ into the barrel to maintain optimal levels. It would also be desirable to not have to perform frequent calibrations of the equipment in the sulfite measurement operation.

SUMMARY OF THE INVENTION

A method of measuring an absorption coefficient of a medium, such as a gas or a liquid, for example, wine or other alcohol, across a light spectrum of wavelengths of a light ray is described. The user of the apparatus containing the optical sensor of the present invention sets an initial or first optical path length L1 as the total length a light ray traverses the medium. For this length L1, first light output intensity values are measured, one for each wavelength of interest across a spectrum of the light ray. This creates a first light output intensity value data set. The user then sets a second optical path length L2 as the total length the light ray traverses the medium. As with L1, for the second length, second light output intensity values are measured, one for each wavelength of interest across the spectrum. This creates a second light output intensity value data set. A processing means then calculates the natural log for each light output intensity from the first light output intensity value data set. This creates a third data set. Similarly, the processing means calculates the natural log for each light output intensity from the second light output intensity value data set, thereby creating a fourth data set. Data from the third and fourth data sets are fitted to a line on a graph where the slope of the line against length provides the absorption coefficient of the medium. In this process, certain optical sensor and related variables are used and all are independent of lengths L1, L2 and other lengths and the absorption coefficient is calculated independently of any of the variables. Finally, the absorption coefficient is calculated in a manner such that drift and variation of a variable over time, outside the time of measurement, have no ramifications on the absorption coefficient calculation.

This greatly reduces if not eliminates the need to calibrate the optical sensor and still obtain accurate absorption coefficient measurements.

In another aspect of the present invention, an optical sensor apparatus is described. The sensor design in one embodiment includes a light source for emitting a light ray having an output intensity. There is also a photo detector for measuring the input intensity of the light ray. This input intensity is represented as responsivity, R. A containment space or window is between a lens and, in one embodiment, a corner cube. The length of this space is L, as referred to above, and can be modified using suitable mechanical or other means. In other embodiments, the apparatus design may have mirrors and gradual geometries to accomplish different lengths for testing. The optical sensor can operate, for example, in an aging barrel containing the medium, in a portable device containing a sample, or in a fermentation tank containing the medium.

DETAILED DESCRIPTION

Figure 1:
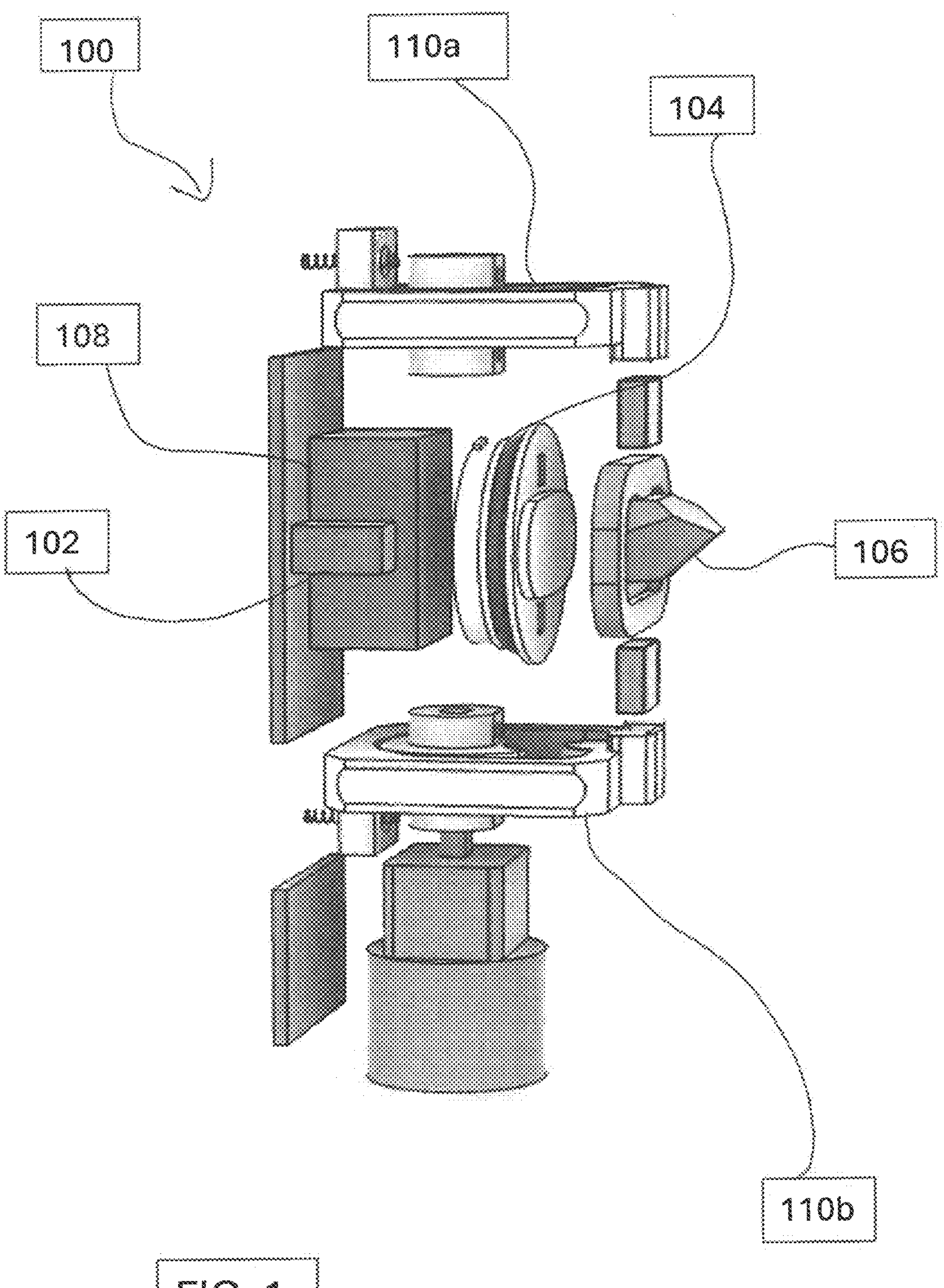
FIG. 1 is a schematic diagram of an optical sensor design in accordance with one embodiment of the present invention.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

The wine barrel closure apparatus of the present invention is, at a basic level, a sensor wine barrel closure that is capable of bidirectional wireless data transmission. More specifically, the apparatus utilizes optical sensing techniques and principles to measure $SO_2$ levels of wine in barrels. And, as described below, the optical transmission and sensor system within the apparatus does not require frequent calibration.

Two components of an optical sensor are a light source and a photo detector. The light source emits light in numerous wavelengths. In order for an optical sensor to provide accurate measurements and readings, it is preferred that it avoid light source (or LED) drift, detector drift, and maintain clean sub-components (windows, lenses, and the like). This leads to the need to calibrate the sensor. With the apparatus and measurement detection methods of the present invention, optical sensor calibration can be bypassed for the purposes of absorption measurements, which leads to sulfite determination.

In the sensor of the present invention, a light source emits a light having an initial intensity (i.e., an intensity "going in" to the liquid or space) and an output intensity coming out where it is detected by a detector with responsivity R. In order to determine sulfite levels in wine, an optical sensor can be used to pass light through wine for a specific distance or length. The detector in the sensor detects an intensity of the light and this can be used as one variable in a method used to calculate absorption. This absorption coefficient can then be used with other values and factors to measure sulfite in the wine.

The optical sensor barrel closure apparatus of the present invention is an elongated cork that is inserted into a barrel thereby sealing the barrel and such that the optical transmission and sensor system of the apparatus is immersed in the wine. Said optical transmission system has a light source which emits a light of intensity $I_{in}$. Light passes through a first containment window with transmission $T_1$. The light then passes through the wine or other medium. In other embodiments the medium may be another type of liquid or may be a gas or solid. The wine has an absorption coefficient $\alpha$. The light transmits through a length, L, of the wine (length of L is dependent on the apparatus sensor component as described below). The light reaches a second containment window with transmission $T_2$, and a final signal is captured by the detector with a responsivity R. The light output intensity detected $I_o$ can be calculated as follows:

$$I_o = I_{in} T_1 e^{-\propto L} T_2 R \qquad \text{Eq1}$$

The variables $I_{in}$ $T_1T_2R$ in Eq1 can be regrouped as B which is independent of length. This results in:

$$I_o = Be^{-\propto L} \qquad \text{Eq2}$$

It is helpful to note that the variables grouped in B are factors that require calibration. However, L, does not. The variable, L, can be purposely adjusted. Continuing with the equations the natural logarithm is taken on both sides which provides Eq3:

$$\ln(I_o) = \ln\left(Be^{-\propto L}\right) \qquad \text{Eq3}$$

This can be represented as Eq4:

$$\ln(I_o) = \ln(B) + \ln\left(e^{-\propto L}\right) \qquad \text{Eq4}$$

And can be further represented as Eq5:

$$\ln(I_o) = \ln(B) - \propto L \qquad \text{Eq5}$$

Equation 5 shows a liner relationship between $\ln(I_o)$ and L, similar to y=mx+b, with ln(B) intercepting the y-axis when L is zero (x-axis being L), and $-\propto$ (minus alpha) being the slope of the line. In one embodiment, the value for B is determined before the apparatus is deployed.

Therefore, taking several measurements of $I_o$ at different lengths L, and fitting $\ln(I_o)$ as a function of L to a line, provides an absorption value $\propto$. This, $\propto$ value is derived completely independent of any of the other factors, such as intensity of the light source, transmission of the windows, or responsivity of the detector.

When a graph of Eq5 is plotted, points on the line correspond to varying L which equates to varying $\ln(I_o)$. When L is zero, y is ln(B). As is evident from Eq5, the slope of the line provides ∝, absorption value. The important point is that the light absorption value can be calculated in a manner where drift and variation in other variables will not affect the slope of the line; it affects only the point where the line intersects the y-axis. In this manner, the value of alpha ∝ has been isolated. Any drift or noise embodied in the optical sensor components are absorbed by ln(B), but does not affect the absorption ∝. Furthermore, an offset in L can also be lumped into ln(B) and the intercept, leaving only the steps of L that need to be precise to obtain an accurate measurement of the absorption ∝.

It is important to note that a detector offset such as dark current could influence the calculation of absorption ∝. Fortunately, even in a compact system such as the described optical sensor, it is simple to obtain a first measurement of the detector with the light source off to obtain the dark current level of the detector and substrate it from the measurements with the light source on and the steps in length. Ambient light could also influence the calculation of absorption ∝ and should be accounted for. However, for the application for the optical sensor inside a wine barrel, this factor can be neglected.

In one embodiment, the other variables $I_{in}$ $T_1T_2R$ (collectively, the noise in the optical sensor apparatus) can be tracked to get the health of the sensor. However, as noted, these variables do not have to be calibrated at time zero. The only factor that needs to be tracked is how absorption ∝ changes as L changes.

In one embodiment, the optical sensor measures various wavelengths. As such, multiple ∝ (absorption rates) can be calculated from one light source per wavelength. Absorption rate ∝ may depend on the wavelength. For $SO_2$, the relevant average wavelength is between 265 nm and 285 nm. This enables the apparatus of the present invention to detect $SO_2$ exclusively or be used to calculate ∝ for other wavelengths which, in turn, can be used to measure other chemicals in the medium. Furthermore, a spectral curve of an absorption coefficient is used to determine other useful properties of the medium. In one embodiment, when testing in a visible spectrum, absorption spectrums can be used to calculate apparent color of the medium (e.g., color of the wine). If testing in the infrared part of the spectrum, absorption data can be used to detect particular chemical bonds in the medium that can help determine the presence of certain substances (including $SO_2$) as each bond has a different absorption peak, thus making it easier to differentiate and separate chemical components.

The light source can be an LED which provides a targeted wavelength distribution. In one embodiment, the light source is on a pedestal in the optical transmission system and can be adjusted to change L (the light source can be moved up or down).

The photo detector can absorb wider wavelength spectrums than the targeted wavelength distribution, but the response will be limited by the spectrum of the illumination. The light source must be focused, and the photo detector must have a wide area, such that the system does not introduce variation in the intensity detected by the movement of the pedestal. Ideally, the photo detector will detect the same intensity, and produce the same amplitude for different lengths L, when no absorption medium is present. If there is a systematic variation with length L, it could be recorded and used to normalize the data received.

In other embodiments, the light source can be a broad band light source, and the photo detector a spectrometer capable of separating and detecting each wavelength individually for more information. The choice of light source and photo detector depend on the spectrum of interest and application constraints. Current technologies such as tungsten based lamps produce broad spectrums from the ultraviolet (UV) around 300 nm to the far infrared around 2.5 um. However, such technologies required specialized electronic drivers, tend to be bulky, and not very energy efficient. Lasers can be produced to emit in a very narrow wavelength and some system can tune the wavelength with some limitations the range. However, these laser based system are costly, bulky and not very efficient. LEDs can be fabricated in different parts of the spectrum, and can also be coated with phosphors to produce a wider spectral range. Violet or blue LEDs can pump white phosphors to produce a spectrum from the violet to the deep red with reasonably good efficacy and in a very compact system. LED can also be fabricated in the infrared and far infrared regions but at the expense of cost and efficiency.

When the sensor is used for the first time, a reading is obtained and tracked overtime by the service provider to determine the condition of the sensor by monitoring B. If B is fluctuating significantly, the provider can be alerted to check the sensor.

FIG. 1 is a schematic diagram of an optical sensor design in accordance with one embodiment of the present invention. An optical sensor 100 shown has a specific design that is suitable, for example, for use in an apparatus that can be inserted into a barrel, such as an aging barrel for wine (the apparatus can be used to seal the barrel). Shown is a light source 102 that emits a light ray having multiple wavelengths. A light ray traverses through a collimating/focusing lens component 104. Once the light ray passes through lens 104 it enters a space or containment window which contains the medium being analyzed. This space or containment window has a length L that can be adjusted using window length adjustment components 110*a* and 110*b*. After passing through the medium, the light ray reaches a corner cube 106 which reflect the light ray in a parallel path and in the opposite direction (not the same path from where the light ray was received at corner cube 106). The length of the containment window is modified by components 110*a* and/or 110*b* by laterally moving corner cube 104. That is, adjustment components 110*a* and 110*b* adjust the length between focusing lens 104 and corner cube 106. As noted, this is one design of an optical sensor. Other embodiments may have additional components that enable the light ray traversal length to be modified in other ways that are known in the art, for example, additional corner cubes or mirrors. Light ray traverses in the opposite direction via corner cube 106 and is received and detected by a photo detector 108. Optical sensor 100 may also include a processing means, such as a microprocessor (not shown), that detects, measures, and stores data (as described herein) related to the traversal of the light ray through the medium.

Figure 2:
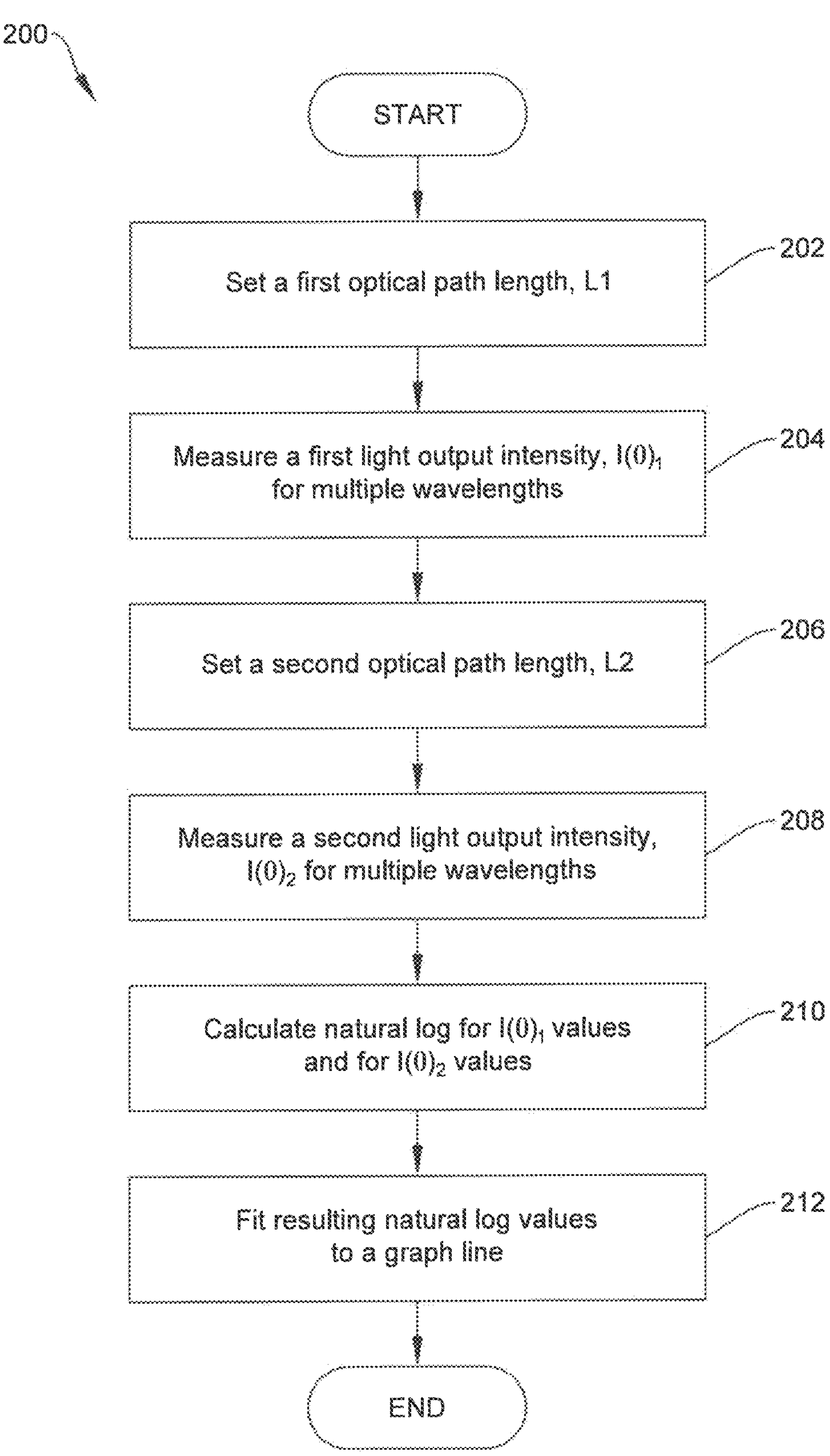
FIG. 2 is a flowchart of a method of determining an absorption coefficient of a medium in accordance with one embodiment of the present invention.

FIG. 2 is a flow diagram showing a method of measuring an absorption coefficient of a medium in accordance with one embodiment of the present invention. It shows at a high level the novel steps described above taken to arrive at an absorption coefficient of a medium. At step 202 the sensor is set to a first optical length, L1. This length can be determined by the user of the apparatus and may depend on various factors such as the medium, light source, objectives of the chemical analysis, and the like. At step 204, the sensor measures a light output intensity for multiple wavelengths for L1. These data are recorded by a processing means in the sensor and stored in a memory. At step 206 the user sets a second optical path length, L2. As noted above, the length of the containment window can be adjusted. At step 208, similar to step 206, measurements of a second light output intensity for multiple wavelengths for length L2 are taken and stored. At step 210 the processing means calculates natural log values of the first light output intensities and calculates natural log values of the second light output intensities. At step 212 the processing means fits these natural log values to a graph line.

The design described in FIG. 1 is suitable for compact and efficient systems that are adequate to apply to sensors inside wine barrels because of size constraints, longevity and cost. However, in other embodiments, the sensor can also be used where these constraints are not as stringent. For example, in a wine cellar operation, it would be advantageous to add an optical sensor to a device that samples the wine from the barrel to provide rich chemical analysis of the wine. Since size, efficiency, and cost are not as restrictive compared to the embodiment where the optical sensor is inside the barrel, more sophisticated light source and spectrometers can be used to produce this more comprehensive chemical analysis. In other embodiments, an optical sensor could be added to fermentation tanks to track the evolution of chemistry during this key stage in the wine making process.

The optical sensor of the described embodiment can be designed in several optical configurations without affecting the methods of determining an absorption coefficient as described herein, including the method described in FIG. 2. The one configuration used is a single pass transmission design. In this design, the light source is at one end, the medium is contained in the middle (e.g., in a containment window) and the photo detector is at the other end. A single ray of light is emitted at the light source, passes through windows and medium to reach the photo detector. In another embodiment, a ray of light can be folded or redirected using a mirror to pass again through the medium before reaching the photo detector. Multiple mirrors can be used to make multiple passes through the medium. These techniques are useful to allow to place the light source and photo detector in more convenient places or increase the optical path length through the medium to increase the absorption signal. In a similar embodiment, the ray can be folded using a corner cube (or multiple corner cubes), such as the one shown in FIG. 1, that allows returning the beam parallel to but spaced apart from the first ray. These optical designs can be used and adapted as needed for the application. In the case of the optical sensor in a barrel (e.g., an aging wine barrel or whiskey barrel), it is mechanically convenient to have the electronics (light source and photo detector) on one side, and have the optical length change by moving an arm holding the corner cube back and forth (where there are no electronics on the moving arm).

What is claimed is:

1. A method of measuring an absorption coefficient of a medium across a light spectrum of wavelengths, the method comprising:

setting a first optical path length L1 as the total length a specific light traverses the medium;

for L1, measuring a first light output intensity $I_{0\_1}$ for each wavelength of interest across a spectrum of said specific light that traverses the medium for length L1, thereby creating a first $I_{0\_1}$ data set;

setting a second optical path length L2 as the total length the specific light traverses the medium;

for L2, measuring a second light output intensity $I_{0\_2}$ for each wavelength of interest across the spectrum of said specific light that traverses the medium for length L2, thereby creating a second $I_{0\_2}$ data set;

calculating the natural log for each $I_0$ from the first $I_{0\_1}$ data set corresponding to length L1, thereby creating a third data set;

calculating the natural log for each $I_0$ from the second $I_{0\_2}$ data set corresponding to length L2, thereby creating a fourth data set; and fitting data from the third data set for each wavelength and data from the fourth data set for each wavelength to a linear function line of the natural log of a light intensity versus length, L, wherein a slope of the linear function line indicates the absorption coefficient of the medium and an intercept point where the linear function line intercepts a vertical axis conveys data relating to one or more variables, wherein the one or more variables are independent of absorption coefficient measurement.

2. A method as recited in claim 1 wherein an offset in length L1 or L2 is independent of arriving at an accurate measurement of the absorption coefficient.

3. A method as recited in claim 1 further comprising:

tracking variables in a set of variables to obtain a maintenance status of the optical sensor.

4. A method as recited in claim 1 wherein a light source emits the specific light has a plurality of wavelengths and is used to measure other chemicals in the medium.

5. A method as recited in claim 1 wherein the absorption coefficient is determined from the slope of the linear function line representing a linear relationship between the natural log of the light intensity and the length, L.

6. A method as recited in claim 1 wherein the medium is one of a gas, a liquid, wine, whiskey, or other alcohol.

7. A method as recited in claim 1 further comprising:

setting a third optical path length L3 being the third total length the specific light traverses the medium; and for L3, measuring a third light output intensity $I_{0\_3}$ for each wavelength of interest across a spectrum of said specific light that traverses the medium for length L3, thereby creating a third $I_{0\_3}$ data set.

8. A method as recited in claim 1 wherein a set of variables includes an input light intensity, $I_i$, a first transmission time T1, a second transmission time T2 and a responsivity, R, of a photo detector in an optical sensor.

9. A method as recited in claim 8 wherein one or more variables in the set of variables require calibration.

* * * * *